(12) United States Patent
Hu et al.

(10) Patent No.: US 7,087,739 B2
(45) Date of Patent: Aug. 8, 2006

(54) NUCLEIC ACID ENCODING RECOMBINANT SALMON CALCITONIN, EXPRESSION VECTOR THEREOF, AND METHOD FOR PRODUCING RECOMBINANT SALMON CALCITONIN THEREWITH

(75) Inventors: Shuai-Jan Hu, Taipei (TW); Tzu-Chih Chen, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 275 days.

(21) Appl. No.: 10/737,482

(22) Filed: Dec. 16, 2003

(65) Prior Publication Data

US 2004/0132138 A1    Jul. 8, 2004

(30) Foreign Application Priority Data

Dec. 30, 2002    (TW) ............................ 91137839 A

(51) Int. Cl.
*C07H 21/04* (2006.01)
*C12N 15/09* (2006.01)

(52) U.S. Cl. ............ 536/23.5; 435/320.1; 435/69.4; 435/254.21; 530/307

(58) Field of Classification Search ............ 435/69.4, 435/254.21, 320.1; 536/23.5; 530/307
See application file for complete search history.

(56) References Cited

U.S. PATENT DOCUMENTS 6,210,925 B1    4/2001    Mahta et al. ............ 435/69.1

OTHER PUBLICATIONS

Secretion of Oligomeric Val$^8$-human Calcitonin by *Saccharomyces Cerevisiae* Mironova et al.; 1991.
Production of Bioactive Salmon Calcitonin From the Nonendocrine Cell Lines COS-7 and CHO Takahashi et al.; 1996.

*Primary Examiner*—Chih-Min Kam
(74) *Attorney, Agent, or Firm*—Thomas, Kayden, Horstemeyer & Risley

(57) ABSTRACT

Nucleic acid encoding recombinant salmon calcitonin, expression vector thereof, and method for producing recombinant salmon calcitonin therewith. The nucleic acid encoding recombinant salmon calcitonin comprises the sequence of SEQ ID No. 2.

8 Claims, 7 Drawing Sheets

SEQUENCE LISTING

<160> NUMBER OF SEQ ID NOS: 7

<210> SEQ ID NO 1
<211> LENGTH: 96
<212> TYPE: DNA
<213> ORGANISM: Oncorhynchus gorbuscha
<300> PUBLICATION INFORMATION:
<301> AUTHORS: Martial, K., Maubras, L., Taboulet, J., Jullienne,
       A., Milhaud,
       G., Moukhtar, M.S. and Cressent, M
<302> TITLE: Production of salmon calcitonin I in Oncorhynchus
       gorbuscha by
<303> JOURNAL: Gene
<304> VOLUME: 149
<305> ISSUE: 2
<306> PAGES: 277-281
<307> DATE: 1994-11-18
<313> RELEVANT RESIDUES: (16)..(111)

<400> SEQUENCE: 1
tgctccaacc tcagcacctg tgtgctgggc aaactgtccc aagagctgca caaattgcag    60
acgtaccccc gcaccaacac gggaagtggc acgcct                              96

<210> SEQ ID NO 2
<211> LENGTH: 96
<212> TYPE: DNA
<213> ORGANISM: artificial
<220> FEATURE:
<223> OTHER INFORMATION: modified to be suitable for salmon calcitonin
       expression in yeast

<400> SEQUENCE: 2
tgttctaatt tgtctacttg tgttctaggt aaattatcac aagaattaca taaattgcag    60
acttatccaa gaaccaatac aggttcagga cacct                               96

<210> SEQ ID NO 3
<211> LENGTH: 60
<212> TYPE: DNA
<213> ORGANISM: artificial
<220> FEATURE:
<223> OTHER INFORMATION: primer

<400> SEQUENCE: 3
tgtggtaatt tgtctacttg tatgttaggt acatataccc aagattttaa taaattccat    60

<210> SEQ ID NO 4
<211> LENGTH: 60
<212> TYPE: DNA
<213> ORGANISM: artificial
<220> FEATURE:
<223> OTHER INFORMATION: primer

<400> SEQUENCE: 4
aggtgcgcca actccaatag cagtttgtgg aaatgtatgg aatttattaa atcttgggt    60

<210> SEQ ID NO 5
<211> LENGTH: 60
<212> TYPE: DNA
<213> ORGANISM: artificial
<220> FEATURE:
<223> OTHER INFORMATION: primer

<400> SEQUENCE: 5
tgttctaatt tgtctacttg tgttctaggt aaattatcac aagaattaca taaattgcag    60

```
<210> SEQ ID NO 6
<211> LENGTH: 60
<212> TYPE: DNA
<213> ORGANISM: artificial
<220> FEATURE:
<223> OTHER INFORMATION: primer

<400> SEQUENCE: 6
aggtgttcct gaacctgtat tggttcttgg ataagtctgc aatttatgta attcttgtga      60

<210> SEQ ID NO 7
<211> LENGTH: 32
<212> TYPE: PRT
<213> ORGANISM: Oncorhynchus gorbuscha
<300> PUBLICATION INFORMATION:
<301> AUTHORS: Martial, K., Maubras, L., Taboulet, J., Jullienne,
      A., Milhaud,
      G., Moukhtar, M.S. and Cressent, M
<302> TITLE: Production of salmon calcitonin I in Oncorhynchus gorbuscha
      by alternative polyadenylation of two RNA species
<303> JOURNAL: Gene
<304> VOLUME: 149
<305> ISSUE: 2
<306> PAGES: 277-81
<307> DATE: 1994-11-18
<313> RELEVANT RESIDUES: (6)..(37)

<400> SEQUENCE: 7

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30
```

NUCLEIC ACID ENCODING RECOMBINANT SALMON CALCITONIN, EXPRESSION VECTOR THEREOF, AND METHOD FOR PRODUCING RECOMBINANT SALMON CALCITONIN THEREWITH

BACKGROUND OF THE INVENTION

1. Field of the Invention

The present invention relates to calcitonin (CT). More particularly, the present invention relates to the expression of calcitonin in yeasts.

2. Description of the Related Arts

Calcitonin was identified as a hormone factor for reducing the concentration of calcium ion in serum in 1962. It was also noted that calcitonin is secreted by C-cells from the thyroid gland. Busolati G et al. (1967) proposed that calcitonin is composed of 32 amino acids, the first and the seventh cysteines have a disulfide bond, and proline at the C-terminal end is amidated. Sexton, P. M. et al. (1999) reported that the amidation of proline at the C-terminal end is critical for the bioactivity of calcitonin. In vitro study by Sexton, P. M. et al. (1983) and in vivo study by Chamber, T. J. et al. (1983) have demonstrated that the adenylyl cyclase and cAMP dependent protein kinase can be activated by the binding of calcitonin and calcitonin receptor on cell membrane to decrease osteoclast activity thereby alleviating osteoporosis. It is known that calcitonin anticipates calcium ion metabolism and inhibits osteoporosis resulting from osteoclast activity; therefore, calcitonin is considered an effective agent for the treatment of osteoporosis.

Gennari, C. et al. (1999) and Avioli, L. V. (1997) reported that calcitonin provides both a treatment and a preventive effect. Calcitonin can be used clinically to treat bone disorders, such as Paget's disease, osteoporosis, hypercalcemia malignancy. At present, the clinically used calcitonin is derived from human, salmon, porcine, and eel. Sexton, P. M. et al. (1999) reported that the bioactivity of calcitonin derived from salmon is especially high compared to other sources. The present clinically used calcitonin is manufactured through chemical synthesis, which is costly and limited by the length of amino acids. With the development of molecular technology in the last decade, a trend of protein drug production using living organisms (Ivanov, I. 1987; Ishikawa, H. 1996; 1999) has been arisen.

The present technology using recombinant proteins to produce calcitonin can be classified as *Escherichia coli* production, animal cell production, and yeast production. The advantages and disadvantages of the three productions are discussed in the following.

U.S. Pat. No. 6,210,925B2 to Unigene Laboratories, Inc. discloses a method for calcitonin production by *E. coli* having the advantage of high production; however, the formation of inclusion bodies in *E. coli* decreases the solubility of calcitonin.

Takahashi K. I. et al. (Peptides, 1997; 18(3):439–444) disclose a method for calcitonin production by nonendocrine animal cell lines, such as COS-7 and CHO. The last amino acid of the precursor of recombinant calcitonin is glycine which can be amidated easily and the product is identical to naturally occurring calcitonin without any chemical modification. The disadvantages of this method include low production rate and high cost.

Micronova R. et al. (FEMS Microbiology Letter, 1991; 67(1):23–28) disclose a method for human calcitonin production by *Saccharomyces cerevisiae*. The product can be secreted to the medium and any purification process is unnecessary. The production rate in yeast is between the rates of animal cells and *E. coli*, however, an additional C terminal amidation is necessary.

The above mentioned methods have several disadvantage, hence there is still a need for calcitonin production with high production rate and simple purification process.

SUMMARY OF THE INVENTION

It is therefore a primary object of the present invention to provide an optimized calcitonin DNA sequence back-translated from a modified calcitonin amino acid sequence in accordance with the codon usage of *Saccharomyces cerevisiae* to obtain optimized calcitonin expression in yeasts.

Accordingly, one aspect of the present invention features a separate nucleic acid encoding recombinant salmon calcitonin, comprising a nucleotide sequence of SEQ ID No. 2.

The second aspect of the present invention features an expression vector of recombinant calcitonin, comprising a nucleotide sequence of recombinant salmon calcitonin as shown in SEQ ID No. 2.

In another aspect of the present invention, a method for the production of recombinant calcitonin is provided. The method includes the steps of introducing the above expression vector of recombinant calcitonin into a cell, culturing the cell under a condition suitable for the expression of the recombinant calcitonin, and collecting and purifying the recombinant calcitonin.

BRIEF DESCRIPTION OF THE DRAWINGS

The present invention will be more fully understood and further advantages will become apparent when reference is made to the following description of the invention and the accompanying drawings in which:

FIG. 4A represents the electrophoresis result of the expression in DY150-1 and DY150-2; FIG. 4B represents the electrophoresis result of the expression in CK16-1 and CK16-2, and the block underneath represents the activity of the fusion protein. M represents molecular weight marker, the left arrow indicates 66KD and 55KD, and the right arrow indicates 57KD which is the molecular weight of the fusion protein in the invention.

DETAILED DESCRIPTION OF THE INVENTION

Figure 1:
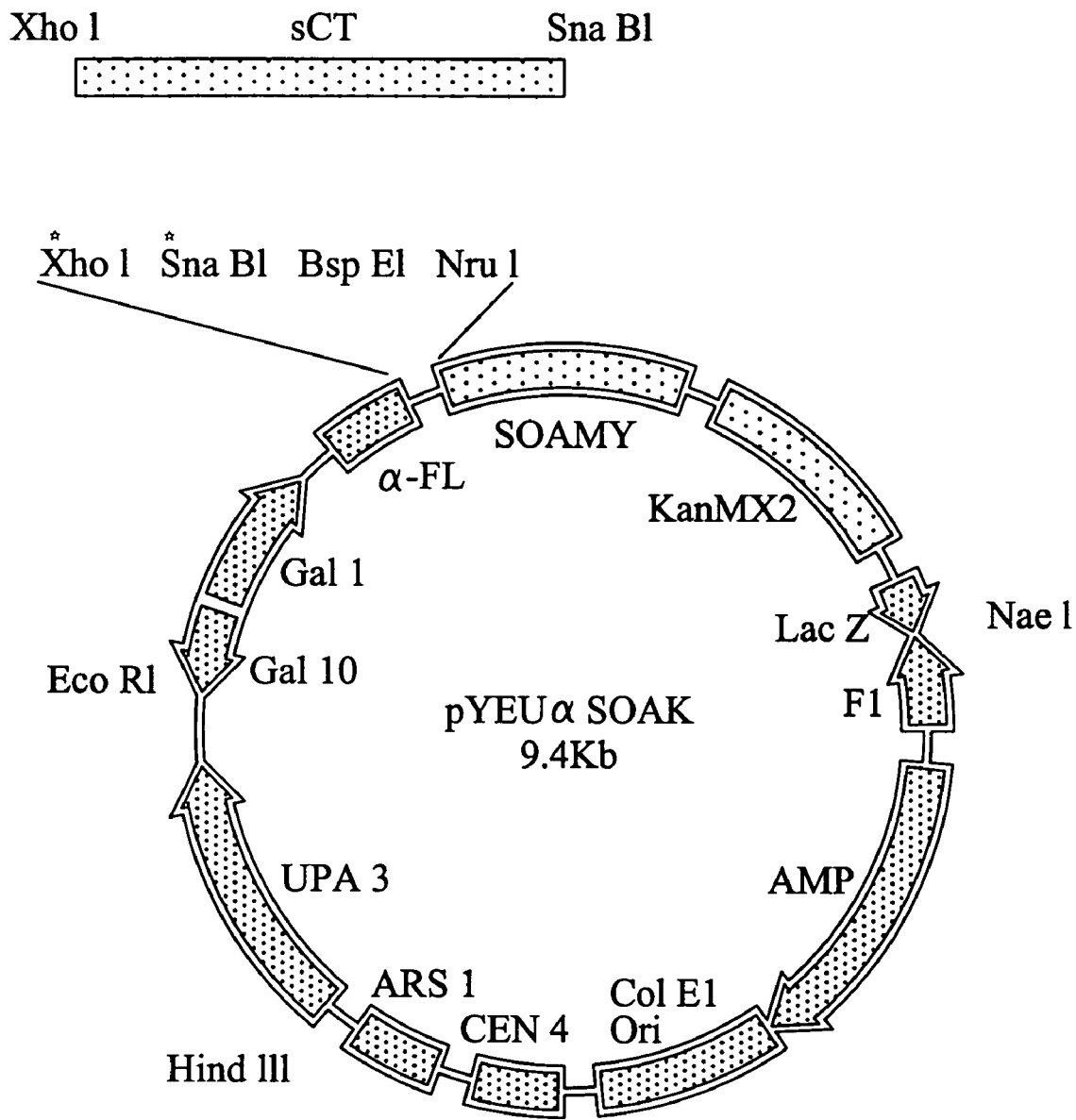
FIG. 1 is a diagram illustrating a one-copied expression vector (pYEUαSOAK) and the inserted fragment (sCT) in the example of the invention.

Without intending to limit the invention in any way, the present invention will be further illustrated by the following description.

Calcitonin is a hormone protein with a short peptide composed of 32 amino acids. The molecular weight of calcitonin is too small to be analyzed by protein electrophoresis since it cannot be stained easily and may be mixed with small-molecular short-peptides in the bacterial broth. In addition, the bioactivity of calcitonin has to be demonstrated via complicated osteoblast cell culture or animal experiment. The invention provides a simple method for the preparation of calcitonin with a yeast expression vector ligated with an artificial calcitonin designed from naturally occurring salmon calcitonin.

The naturally occurring salmon calcitonin nucleotide sequence designated as S74353 in GENEBANK are shown as below:

```
                                              (SEQ ID No. 1)
TGC TCC AAC CTC AGC ACC TGT GTG CTG GGC
Cys Ser Asn Leu Ser Thr Cys Val Leu Gly 10

AAA CTG TCC CAA GAG CTG CAC AAA TTG CAG
Lys Leu Ser Gln Glu Leu His Lys Leu Gln 20

ACG TAC CCC CGC ACC AAC ACG GGA AGT GGC
Thr Tyr Pro Arg Thr Asn Thr Gly Ser Gly 30

ACG CCT
Thr Pro                                   32
```

In view of the amino acid sequence of calcitonin, it is noted that the sequence of salmon calcitonin has 6 high usage codons and 26 low usage codons in accordance with the codon usage table of *Saccharomyces cerevisiae* as shown in table 1.

TABLE 1

The codon usage of *Saccharomyces cerevisiae*

| Ala | GCT 0.37 | GCA 0.30 | Pro | CCA 0.41 | CCT 0.31 |
|-----|----------|----------|-----|----------|----------|
|     | GCC 0.22 | GCG 0.11 |     | CCC 0.16 | CCG 0.12 |
| Arg | AGA 0.47 | AGG 0.21 | Leu | TTG 0.28 | TTA 0.28 |
|     | CGT 0.14 | CGA 0.07 |     | CTA 0.14 | CTT 0.13 |
|     | CGC 0.06 | CGG 0.04 |     | CTG 0.11 | CTC 0.06 |
| Asn | AAT 0.60 | AAC 0.40 | Lys | AAA 0.58 | AAG 0.42 |
| Asp | GAT 0.65 | GAC 0.35 | Met | ATG 1.0  |          |
| Cys | TGT 0.62 | TGC 0.38 | Phe | TTT 0.59 | TTC 0.41 |
| Gln | CAA 0.68 | CAG 0.32 | Trp | TGG 1.0  |          |
| Glu | GAA 0.70 | GAG 0.30 | Tyr | TAT 0.57 | TAC 0.43 |

TABLE 1-continued

The codon usage of *Saccharomyces cerevisiae*

| Gly | GGT 0.45 |          | Ser | TCT 0.26 | TCA 0.21 |
|-----|----------|----------|-----|----------|----------|
|     | GGA 0.23 | GGC 0.20 |     | TCC 0.16 | AGT 0.16 |
|     | GGG 0.12 |          |     | TCG 0.10 | AGC 0.11 |
| His | CAT 0.64 | CAC 0.36 | Thr | ACT 0.34 | ACA 0.31 |
|     |          |          |     | ACC 0.21 | ACG 0.14 |
| Ile | ATT 0.46 |          | Val | GTT 0.39 | GTA 0.22 |
|     | ATA 0.28 | ATC 0.26 |     | GTC 0.20 | GTG 0.20 |

The salmon calcitonin nucleotide sequence was designed by modifying the codons with low usage rate to have a high usage rate, and the expression of calcitonin in yeasts was then optimized.

The resulting recombinant salmon calcitonin nucleotide sequence of the invention is shown as below:

```
                                              (SEQ ID No. 2)
TGT TCT AAT TTG TCT ACT TGT GTT CTA GGT
Cys Ser Asn Leu Ser Thr Cys Val Leu Gly 10

AAA TTA TCA CAA GAA TTA CAT AAA TTG CAG
Lys Leu Ser Gln Glu Leu His Lys Leu Gln 20

ACT TAT CCA AGA ACC AAT ACA GGT TCA GGA
Thr Tyr Pro Arg Thr Asn Thr Gly Ser Gly 30

ACA CCT
Thr Pro                                   32
```

In addition, a recombinant expression vector for the extracellular secretion of calcitonin fusion protein was constructed. It is noted that calcitonin has an amino acid sequence "Asn-x-Thr/Ser" which may be modified by glycosylation. The glycosylation of this sequence may change the molecular weight and antigenicity of calcitonin and the secreted calcitonin will then be undetectable and cannot be used. To avoid the possible glycosylation of this amino acid sequence during the yeast secretion process, mutant strains with low glycosylation is applied. Moreover, the detection of calcitonin produced from yeasts includes calcitonin antibody detection or the detection of the fusion protein activity. When a suitable expression vector and suitable transformed strains are selected, the expression vector can be constructed again to express calcitonin alone.

Therefore, the invention features an expression vector of a recombinant salmon calcitonin comprising a recombinant salmon calcitonin gene of SEQ ID No. 2. In a preferred embodiment, the expression vector is pYEUαSOAK-sCT.

Another aspect of the invention features a method of producing a recombinant calcitonin, comprising the steps of: introducing the expression vector of the recombinant salmon calcitonin into a cell, culturing the cell in a condition suitable for the expression of the recombinant calcitonin, and collecting and purifying the recombinant calcitonin.

Practical examples are described herein.

EXAMPLE

Example 1

Synthesis of a Full-length Calcitonin by Gene Combination

First, the full-length calcitonin was designed in accordance with the codon usage table of *Saccharomyces cerevisiae* to be shown as the sequence of SEQ ID No.2. Two primers of about 60 bp were also designed for the sequence. The two primers sharing 20 bp complementary nucleotides are shown as below.

```
TGT GGT AAT TTG TCT ACT TGT ATG TTA GGT ACA TAT ACC CAA   (SEQ ID No. 3)
GAT TTT AAT AAA TTC CAT

AGG TGC GCC AAC TCC AAT AGC AGT TTG TGG AAA TGT ATG GAA   (SEQ ID No. 4)
TTT ATT AAA ATC TTG GGT
```

The full-length calcitonin was synthesized by PCR. The 50 μl of reaction solution includes 1 μl each of the two primers (0.1 μg/μl), 4 μl of 2.5 mM dNTPs, 5 μl of 10× Taq Plus buffer, 1 μl of 3 U/μl Taq-Pfu and 38 μl of ddH$_2$O. The reaction was performed in a Gene Amp PCR system 2400 (Perkin Elmer) under a condition of: 1 cycle of 98° C. for 5 min, 30 cycles of 98° C. for 2 min, 60° C. for 2 min, 72° C. for 2 min, and a final cycle of 72° C. for 5 min. The PCR product is the full-length calcitonin gene.

The PCR product was used as the template for the second PCR to synthesize calcitonin with restriction sites. Two primers were designed to include XhoI and SnaBI sites, as shown below:

```
TGT TCT AAT TTG TCT ACT TGT GTT CTA GGT AAA TTA TCA CAA   (SEQ ID No. 5)
GAA TTA CAT AAATTG CAG

AGG TGT TCC TGA ACC TGT ATT GGT TCT TGG ATA AGT CTG CAA   (SEQ ID No. 6)
TTTATG TAA TTC TTG TGA
```

The 50 μl of reaction solution includes 2.4 μl of the first PCR product, 1 μl each of the two primers (0.5 μg/μl), 2 μl of 2.5 mM dNTPs, 5 μl of 10× Taq Plus buffer, 1 μl of 3 U/μl Taq-Pfu enzyme and 27.6 μl of ddH$_2$O. The reaction was performed in a Gene Amp PCR system 2400 (Perkin Elmer) under a condition of: 1 cycle of 98° C. for 5 min, 25 cycles of 98° C. for 1 min, 60° C. for 1 min, 72° C. for 1 min, and a final cycle of 72° C. for 5 min. The PCR product is the calcitonin gene with XhoI and SnaBI restriction sites.

Example 2

The Construction of a Expression Vector for sCT:::SOAMY Secretion

The vector named as pYEUαSOAK (Yeastern Biotech Co., Ltd., Taiwan) was constructed to include centromere (CEN4) and autonomous replicative sequence (ARS). The vector has a length of 9.4 kb and includes an amylase gene SOAMY with a secretion signal αFL. The map of the vector is shown in FIG. 1. The vector is a circular molecule and can be simultaneously replicated with the yeast chromosome to maintain 1–3 vector molecules for each yeast cell. With this system, the physiology and metabolism of the host cell are not influenced by high intracellular molecules, and the exogenous protein produced in the host cell will not damage the entire host cell. The preferred host cell or vector can be then selected more objectively.

The detailed construction is shown in FIG. 1. The salmon calcitonin (sCT) was inserted into pYEUαSAOK to form a fusion gene of α-FL:::sCT:::SOAMY. The procedure is recited below. The calcitonin gene fragment with XhoI and SnaBI restriction sites obtained from EXAMPLE 1 and pYEUαSAOK were digested separately. The XhoI digestion was performed first. 50 μl of pYEUαSOAK(1 μg) was added with 2 μl of XhoI(20 U), 0.6 μl of BSA(10 mg/ml), 6 μl of 10× buffer, and 1.4 μl of ddH$_2$O to form a total volume of 60 μl. 35 μl of the calcitonin gene fragment obtained from EXAMPLE 1 was added with 2 μl of XhoI (20 U), 0.45 μl of BSA(10 mg/ml), 6 μl of 10× buffer, and 3.05 μl of ddH$_2$O to form a total volume of 45 μl. The two reactions were incubated at 37° C. for 16 hours, and SnaBI digestion was then performed. 60 μl of the digested pYEUαSOAK was added with 4 μl of SnaBI (20 U), 0.1 μl of BSA (10 mg/ml), 1 μl of 10× buffer, and 4.9 μl of ddH$_2$O to form a total volume of 70 μl. 45 μl of the digested calcitonin gene fragment was added with 4 μl of SnaBI (20 U), 0.25 μl of BSA (10 mg/ml), 2.5 μl of 10× buffer, and 19.25 μl of ddH$_2$O to form a total volume of 70 μl. The two reactions were incubated at 37° C. for 4 hours. The digested products were purified by a PCR clean-up kit.

Figure 2:
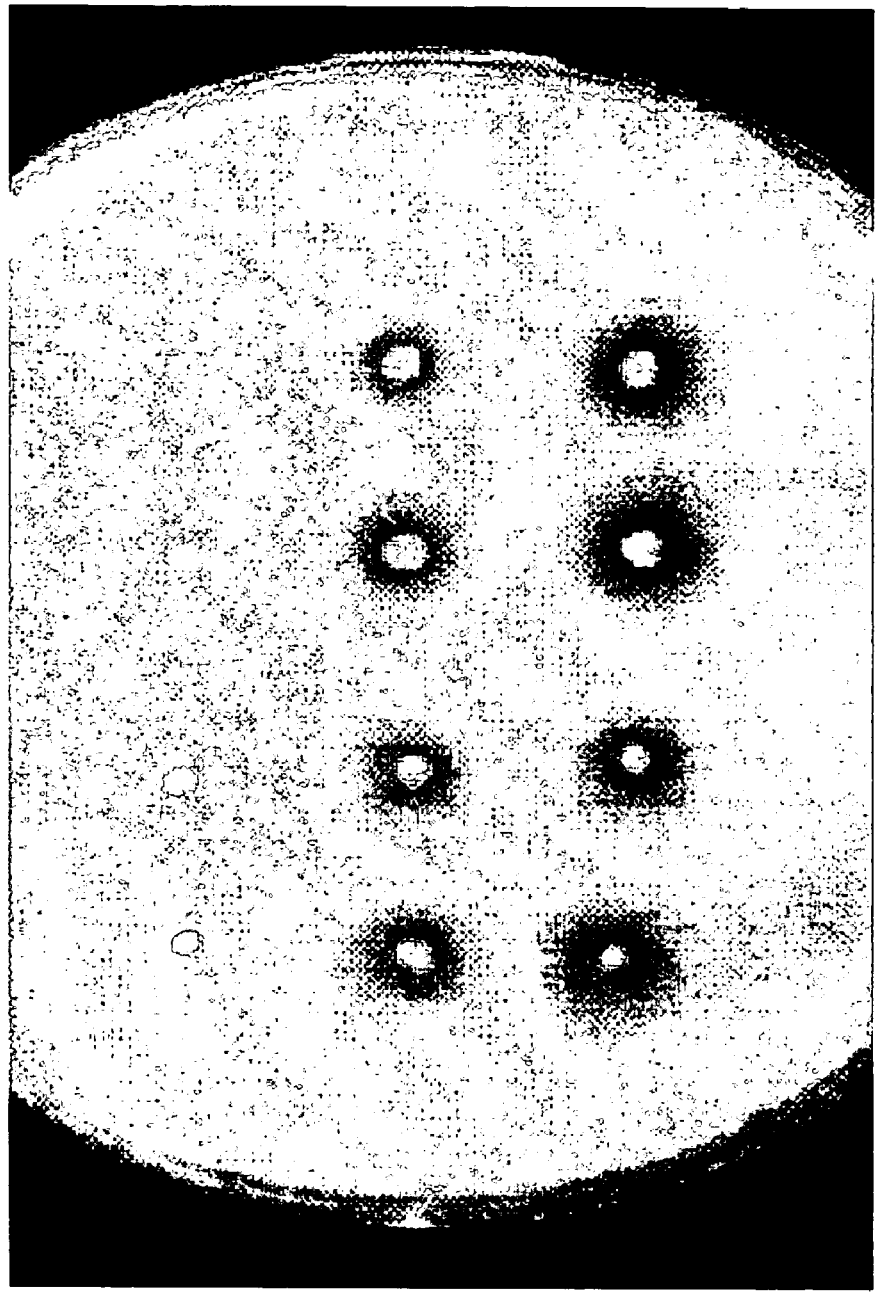
FIG. 2 is a photograph showing the sCT:::SOAMY fusion protein in the example of the invention. The left two lines are the expression in EJ758, and the right two lines are the expression in W303; 1 represents negative control, 2 and 3 represent arbitrarily selected two pYEUαSOAK-sCT.

Ten μl of the ligation reactants included 1 μl of sCT, 1 μl of pYEUαSOAK, 1 μl 10× ligase buffer, 1 μl of ligase, and 6 μl of ddH$_2$O, and the ligation reaction was performed at 16° C. for 12–16 hours. The next step was transformation. 5 μl of ligated product was added into 100 μl of TOP10 competent cell (stratagene). After a 30 min ice bath, 37° C. incubation for 3 min, and a 10 min ice bath, the bacteria were applied onto an LB/Amp medium and incubated at 37° C. for 16 hours. 10–20 colonies on the LB/Amp medium were separately applied to 200 μl of LB/Amp broth and incubated at 37° C. for 1–2 hours. The colony PCR was performed with a total reaction of 25 μl including 1 μl of the culture broth, 0.5 μl each of primer 1 and 2 (20 μM), 1 μl of dNTPs(2.5 mM), 2.5 μl of 10× Taq buffer, 1 μl of Taq(3 U/μl), and 19 μl of ddH$_2$O. The colony PCR was performed in a Gene Amp PCR system 2400 (Perkin Elmer) under a condition of: 1 cycle of 98° C. for 5 min, 25 cycles of 98° C. for 1 min, 55° C. for 1 min, 72° C. for 1 min, and a final cycle of 72° C. for 5 min. The transformant can be confirmed quickly. After sequencing, pYEUαSOAK-sCT was obtained. The vector has GAL1/10 promoter for galactose induction; therefore, the detection of amylolysis acted by SOAMY represents sCT was successfully translated as a part of the fusion protein and secreted into the medium. In addition, the centromere and ARS of the vector provide simultaneously replication with the yeast chromosome and maintain the stability of the vector in the yeast. As shown in FIG. 2, it is confirmed that sCT:::SOAMY was secreted from the transformants cultured in a solid medium with starch. A negative control (1) and two arbitrary pYEUαSOAK-sCT (2 and 3) were transformed into yeasts EJ758 and W303, respectively, and cultured in YNBD medium (leu+Ura+His+Ala+Met) at 28° C. for 2 days. The results show that the α-amylase reaction did not appear in the negative control, but did appear in both transformants of pYEUαSOAK-sCT. In addition, the bacterial growth in the transformants was normal as in the control group. These results confirmed that the sCT:::SOAMY fusion protein from a one-copied expression vector can be secreted in transformants. Next, a multi-copied vector was constructed for better secretion, and suitable strains for large scale secretion were then screened.

Figure 3:
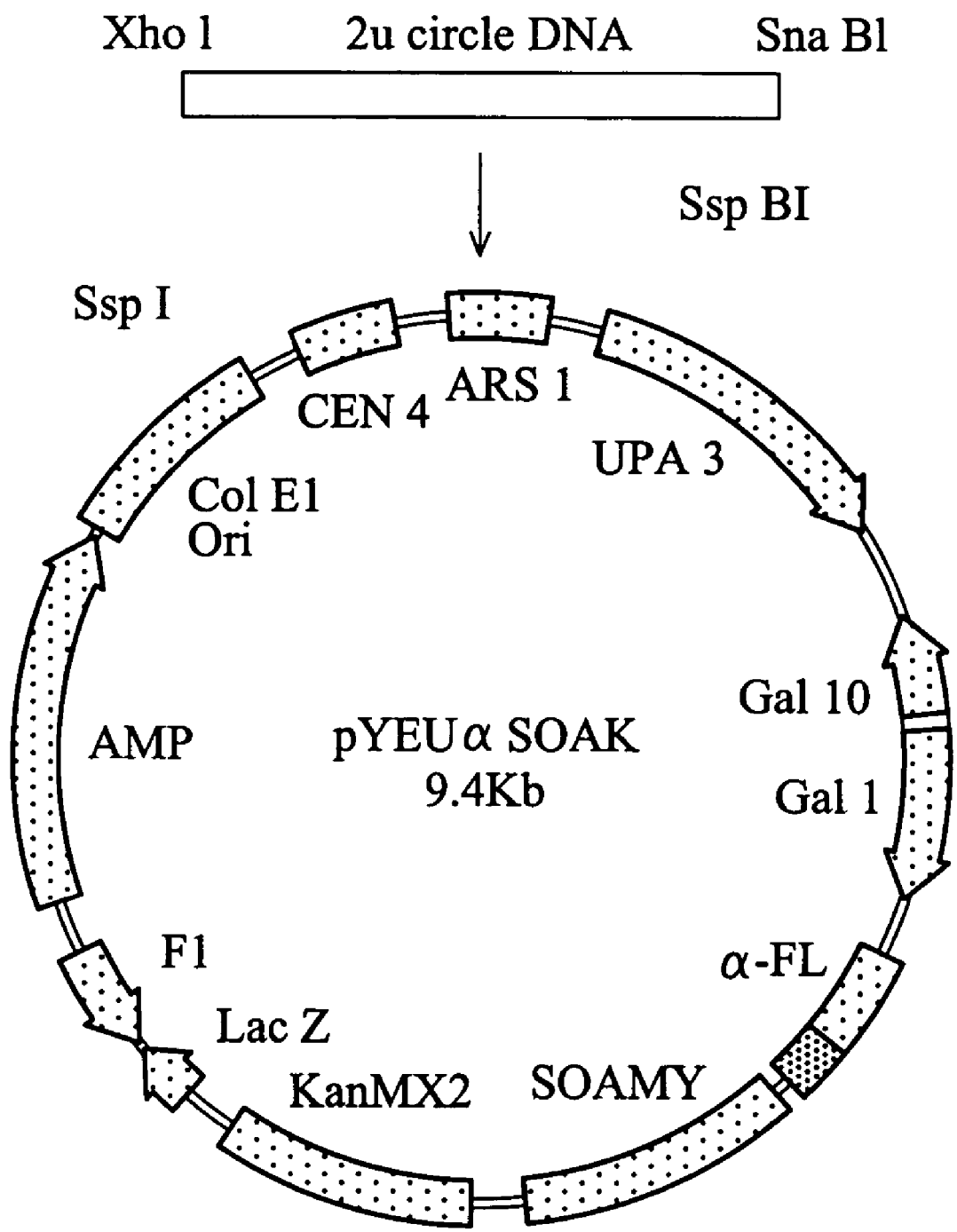
FIG. 3 is a diagram illustrating a multiple-copied expression vector (pYEUUαSOAK) and the inserted fragment (2u circle DNA) in the example of the invention.

As shown in FIG. 3, the expression vector with multiple copies was constructed by replacing CEN-ARS1 with 2μ-ori. The replacement was performed by the restriction sites of SpeI and SspBI. The digestion procedure is similar to the above mentioned steps. The obtained expression vector was designated as pYEUαSOAK2μ-sCT.

Example 3

Figure 4B:
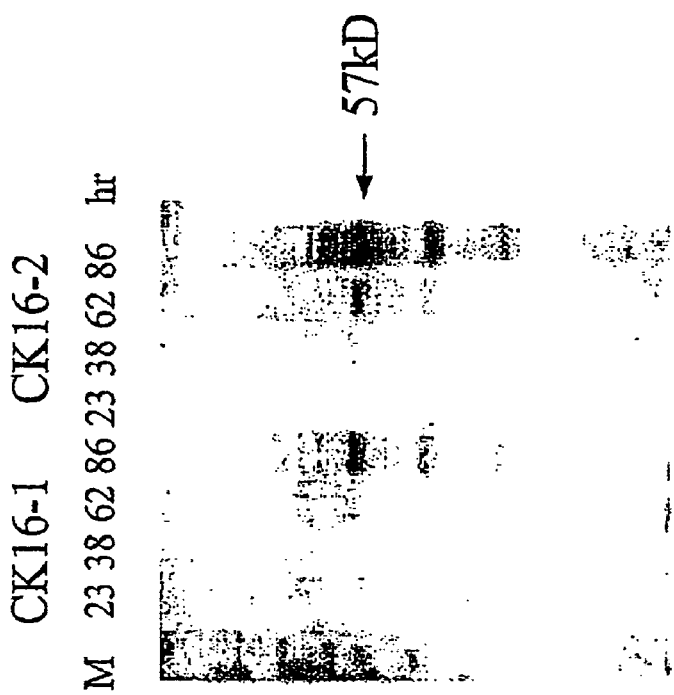
FIGS. 4A and 4B are photographs showing the comparison of CT-amylase fusion protein.
Figure 4A:
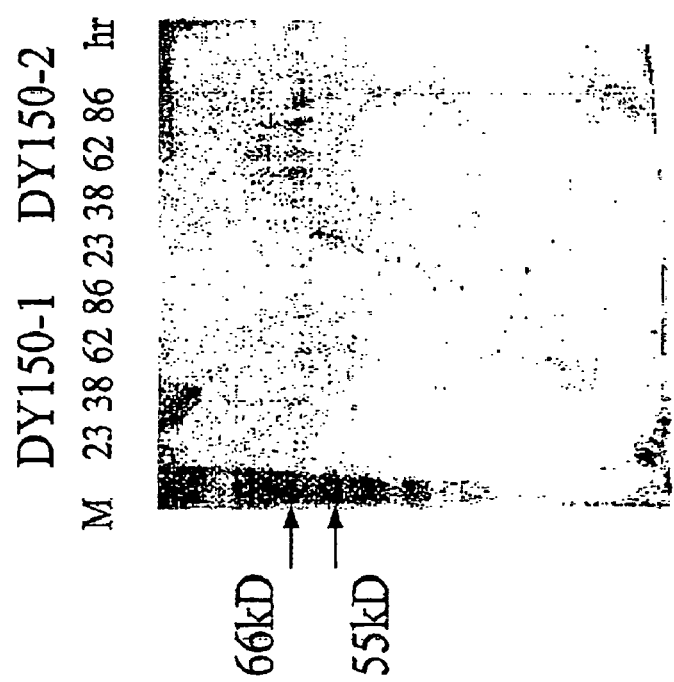

Screening of *Saccharomyces cerevisiae* Strains for sCT:::SOAMY Fusion Protein and Quantification of the Fusion Protein The pYEUαSOAK2μ-sCT obtained by EXAMPLE 2 was transformed into 8 strains of *Saccharomyces cerevisiae* (DY150-1 (Yeastern Biotech Co., Ltd., Taiwan), DY150-2 (Yeastern Biotech Co., Ltd., Taiwan), CK16-1 (Yeastern Biotech Co., Ltd., Taiwan), CK16-2 (Yeastern Biotech Co., Ltd., Taiwan), TL154 (ATCC 96030), AH109 (Clontech com), Y187 (ATCC 96399), and BJ168 (ATCC 4000168)), the strains were cultured in YNBD medium (leu+Ura+His+Ala+Met), and the yeasts were collected at 23, 38, 62, 86 hours. The results were confirmed with SDS-PAGE electrophoresis and coommassie blue staining. It was found that the secretion of the fusion protein in different strains is significantly different as shown in FIGS. 4A and 4B. FIG. 4A shows two mutant strains of a commercialized DY150 strain: DY150-1 and DY150-2, and FIG. 4B shows two mutant strains of CK16 strain which is commonly used for exogenous protein secretion: CK16-1 and CK16-2; the arrow indicates a molecular weight of 57 kD which is the size of the fusion protein in the invention. The results shows that the product secreted by CK16 strains has cumulative ability and the activity of the fusion protein is also cumulative, as shown in the bottom of FIG. 4B.

Figure 5:
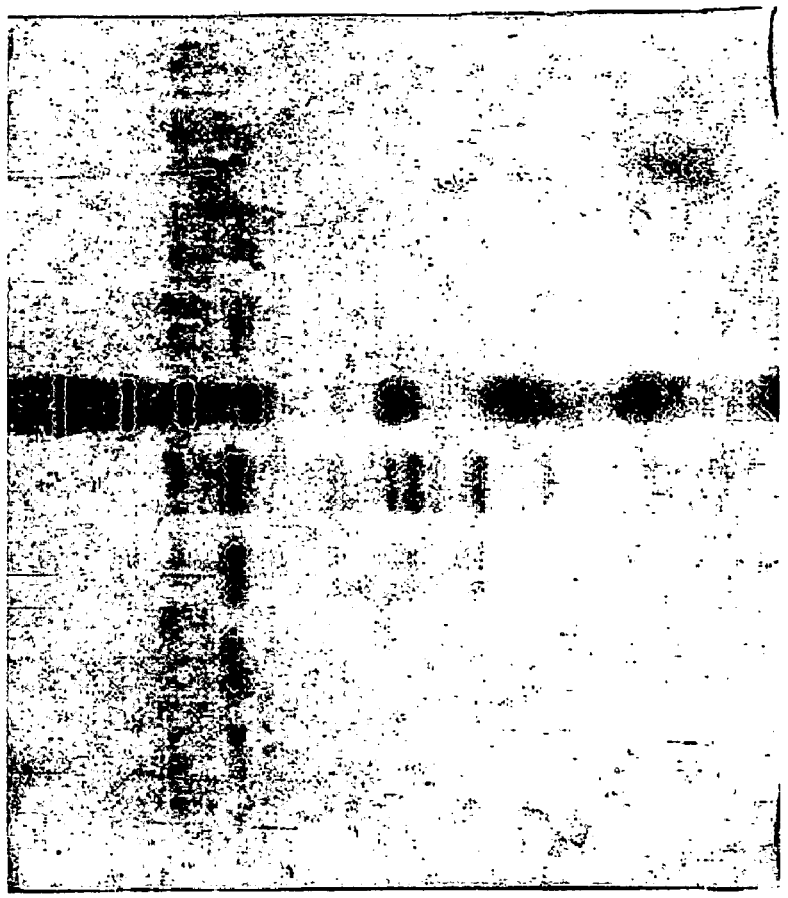
FIG. 5 is a photograph showing the standard quantitative results of the fusion protein and amylase in CK16 after 86 hours. The left four lines are the comparative basis of a standard amylase in 0.5, 1.0, 2.0, and 5.0 μg; the right four lines are the fusion protein of the invention in 0.5, 1.0, 2.0, and 5.0 μg. The calculated production of the invention is about 0.5 μg/5 μg=0.1 g/L.

To determine the quantity of the calcitonin fusion protein, the expression vector of calcitonin fusion protein was transformed to CK16, and the transformed CK16 was cultured for 86 hours and collected. The product was confirmed by SDS-electrophoresis and Coommassie blue staining. The comparative results of the product and standard *Aspergillus* α-amylase (Sigma) are shown as FIG. 5. Lines 1, 2, 3, and 4 represent the standard *Aspergillus* α-amylase diluted to 0.5 μg1.0 μg2.0 μg5.0 μg; lines 5, 6, 7, and 8 represent 86-hour cultured transformed CK16 in 5.0 μl, 2.0 μl, 1.0 μl, and 0.5 μl. The productivity of sCT:::SOAMY fusion protein after 86 hours culturing can be estimated as more than 0.5 μg/5 μl. In the other words, 1 L of transformed yeast may produce more than 100 mg of sCT:::SOAMY fusion protein.

It was found that the influence of different strains on the production of sCT:::SOAMY fusion protein is significant. The commercialized strains such as DY50 have low production rate because the product that experienced over-glycosylation has different molecular weight or is hydrolyzed by protease. This indicates that the genetic influence of strains is important for sCT:::SOAMY fusion protein expression.

Example 4

Figure 6:
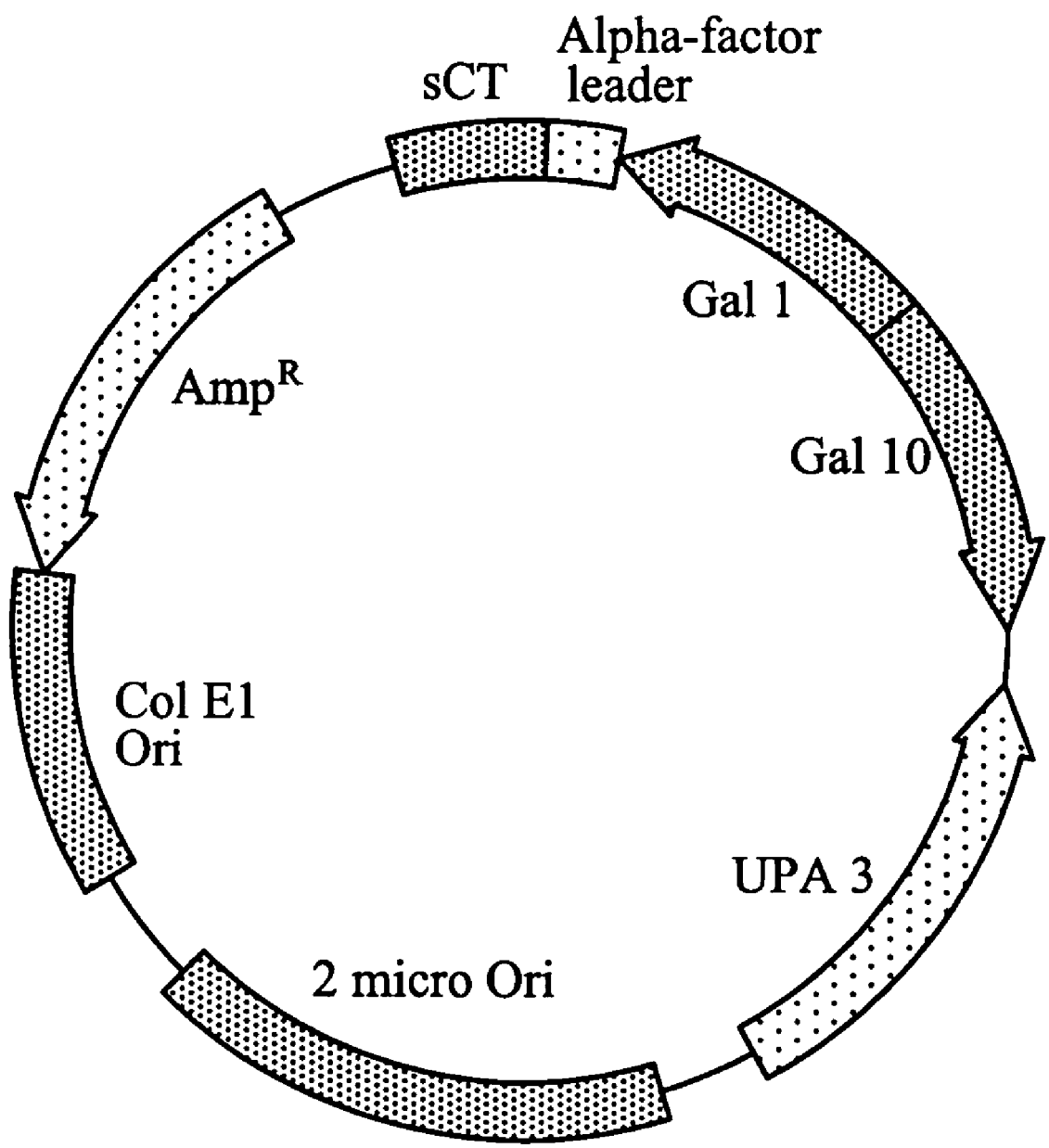
FIG. 6 is a diagram showing the map of pYEUαsCT in the invention.

Construction of YEUαsCT Including sCT Alone and Production of sCT with a Molecular Weight of 4 kd The results of EXAMPLE 3 proved that sCT:::SOAMY fusion protein can be produced. To produce sCT alone, a sCT expression vector without SOAMY was constructed and designated as pYEUαsCT. The map of pYEUαsCT is shown in FIG. 6. The molecular weight of sCT produced from this expression vector is about 4kd.

Figure 7:
FIG. 7 is a photograph showing the comparison of sCT5 secretion in 6 yeast strains. M represents molecular weight marker, + represents positive control, 1 represents CK16, 2 represents DY150, 3 represents AH109, 4 represents TL154, 5 represents Y187, and 6 represents BJ168.

The sCT of 4 kd in pYEUαsCT transformants was determined by silver staining, as shown in FIG. 7. 6 pYEUαsCT transformants, including 1: CK16, 2: DY150, 3: AH109, 4: TL154, 5: Y187, and 6: BJ168, and one positive control (chemically synthesized sCT, "+") are shown in FIG. 7. The results indicate that 1 and 5 produced the predicted product at 4 kd consistent with the molecular weight of the positive control (+). Compared with the positive control, the production rate is about 5 mg/L. Note that the yeasts were not cultured in a fermentor These examples show that the expression vector including the recombinant salmon calcitonin of the invention can be used in a specific *saccharomyces cerevisiae* such as CK16 to produce salmon calcitonin with a high production rate. In addition, the protein produced by *Saccharomyces cerevisiae* is safe. The present chemically synthetic protein has the disadvantages of high cost and is limited by the length of amino acids. The yeast production system of the invention reduces the cost and overcomes the length limitation of chemical synthesis.

While the invention has been particularly shown and described with the reference to the preferred embodiments thereof, it will be understood by those skilled in the art that various changes in form and details may be made without departing from the spirit and scope of the invention.

What is claimed is:

1. An isolated nucleic acid encoding recombinant salmon calcitonin, comprising the nucleotide sequence of SEQ ID NO: 2.

2. An expression vector for recombinant salmon calcitonin comprising the nucleotide sequence of SEQ ID NO:2 encoding a recombinant salmon calcitonin.

3. The expression vector as claimed in claim 2, wherein the vector is pYEUαSOAK-sCT.

4. A method for the production of recombinant salmon calcitonin, comprising the steps of:
   introducing an expression vector as claimed in claim 2 into a cell;
   culturing the cell in a condition suitable for the expression of recombinant salmon calcitonin; and
   collecting and purifying the recombinant salmon calcitonin.

5. The method as claimed in claim 4, wherein the cell is yeast.

6. The method as claimed in claim 4, wherein the cell is *Saccharomyces cerevisiae*.

7. The method as claimed in claim 4, wherein the cell is CK16 strain.

8. The method as claimed in claim 4, wherein the purification step is ion exchange or gel filtration.

* * * * *